United States Patent
Scheinberg et al.

(10) Patent No.: US 6,981,956 B2
(45) Date of Patent: Jan. 3, 2006

(54) WRIST SPLINT

(75) Inventors: Samuel Scheinberg, Otis, OR (US); Adrian A. Polliack, Lake Oswego, OR (US)

(73) Assignee: The Seaberg Company, Inc., Newport, OR (US)

( * ) Notice: Subject to any disclaimer, the term of this patent is extended or adjusted under 35 U.S.C. 154(b) by 534 days.

(21) Appl. No.: 10/357,659

(22) Filed: Feb. 3, 2003

(65) Prior Publication Data
US 2005/0177081 A1 Aug. 11, 2005

(51) Int. Cl.
A61F 5/00 (2006.01)

(52) U.S. Cl. .................. 602/5; 602/20; 602/21

(58) Field of Classification Search ..... 602/4–6,20–23, 602/26–27; 128/877–879, 882
See application file for complete search history.

(56) References Cited

U.S. PATENT DOCUMENTS

| | | | |
|---|---|---|---|
| 3,938,509 A | 2/1976 | Barber | 128/77 |
| 3,943,923 A | 3/1976 | Scheinberg | 128/89 R |
| 4,161,175 A | 7/1979 | Bentele | 128/87 A |
| 4,549,537 A | 10/1985 | Ender | 128/87 A |
| 4,676,233 A | 6/1987 | Scheinberg | 125/87 R |
| 4,677,971 A | 7/1987 | Lindemann | 128/87 R |
| 4,854,309 A | 8/1989 | Elsey | 128/87 R |
| 5,069,203 A | 12/1991 | Anderson | 128/87 R |
| 5,199,941 A | 4/1993 | Makinen | 602/27 |
| 5,417,645 A | 5/1995 | Lemmen | 602/21 |
| 5,419,756 A | 5/1995 | McConnell | 602/36 |
| 5,520,625 A | 5/1996 | Malewicz | 602/21 |
| RE35,290 E | 7/1996 | Druskoczi | 602/18 |
| 5,600,849 A | 2/1997 | Hu | 2/16 |
| 5,601,597 A | 2/1997 | Arrowood et al. | 606/203 |
| 5,685,013 A | 11/1997 | Hausman | 2/16 |
| 5,733,249 A | 3/1998 | Katzin, deceased et al. | 602/21 |
| 5,819,312 A | 10/1998 | Snyder et al. | 2/16 |
| 6,039,706 A | 3/2000 | Bolla et al. | 602/5 |
| 6,106,492 A | 8/2000 | Darcey | 602/8 |
| 6,120,472 A | 9/2000 | Singer, Jr. | 602/64 |
| 6,213,969 B1 | 4/2001 | MacMorran et al. | 602/64 |

FOREIGN PATENT DOCUMENTS

GB 2337704 12/1999

Primary Examiner—Michael Anthony Brown
(74) Attorney, Agent, or Firm—Chernoff, Vilhauer, McClung & Stenzel, LLP

(57) ABSTRACT

A wrist splint with an initially generally planar malleable metal core covered by a layer of synthetic foam padding material on each of its opposite sides and protected by an outer cover of fabric. Depending on the orientation of the splint relative to the patient, the splint provides greater or lesser firmness of support when the core is bent to conform the splint to the patient's hand, wrist, and forearm.

23 Claims, 5 Drawing Sheets

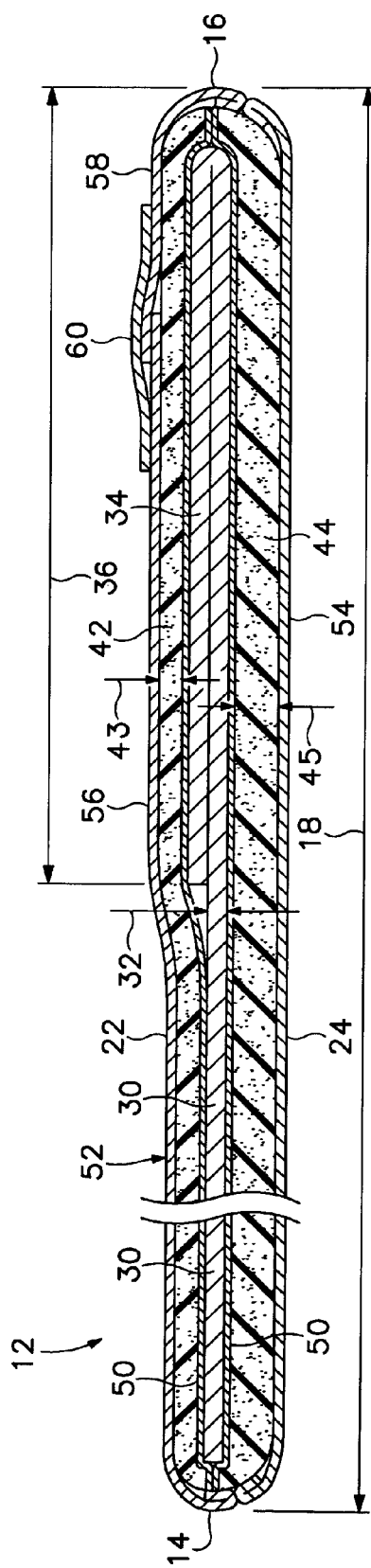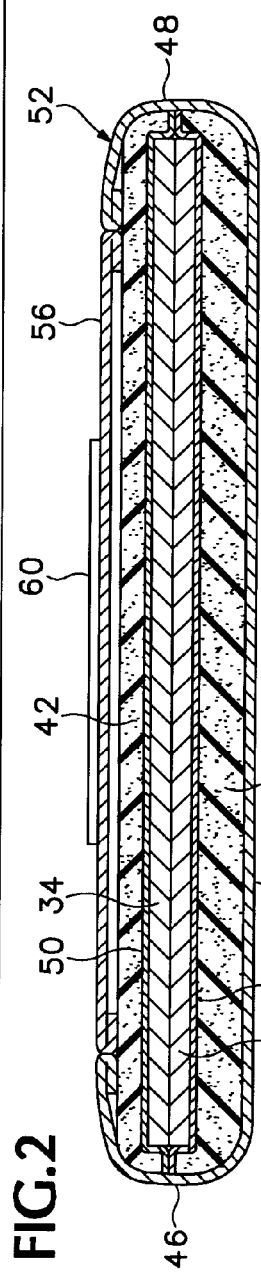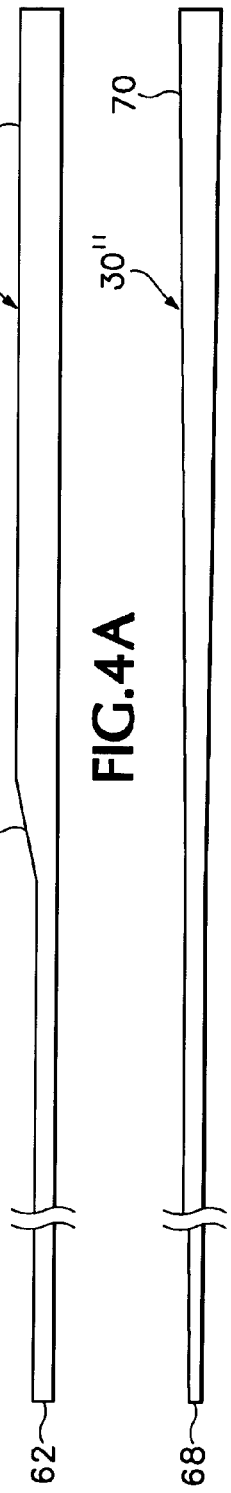
FIG.2
FIG.3
FIG.4A
FIG.4B

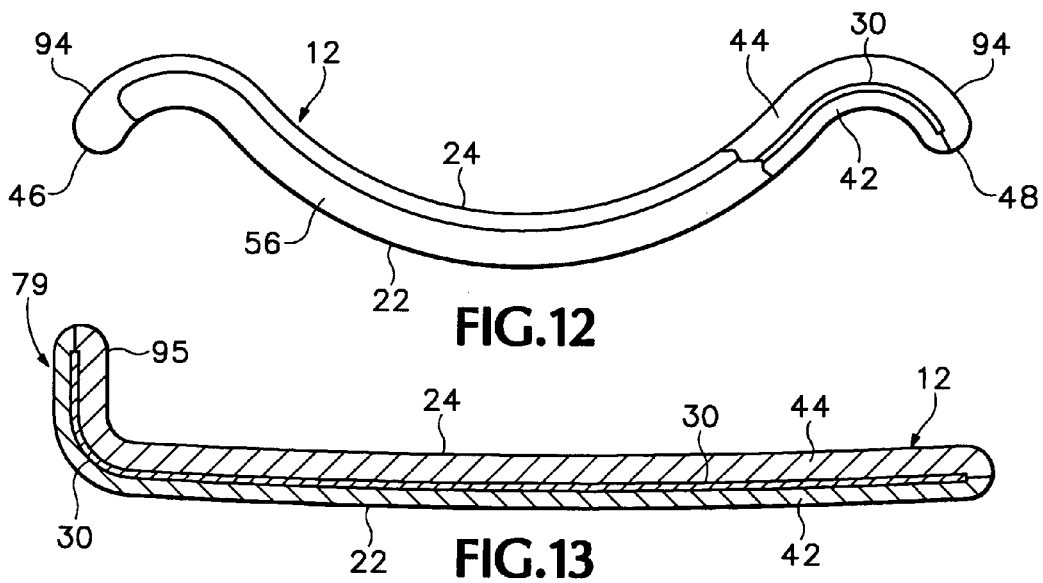
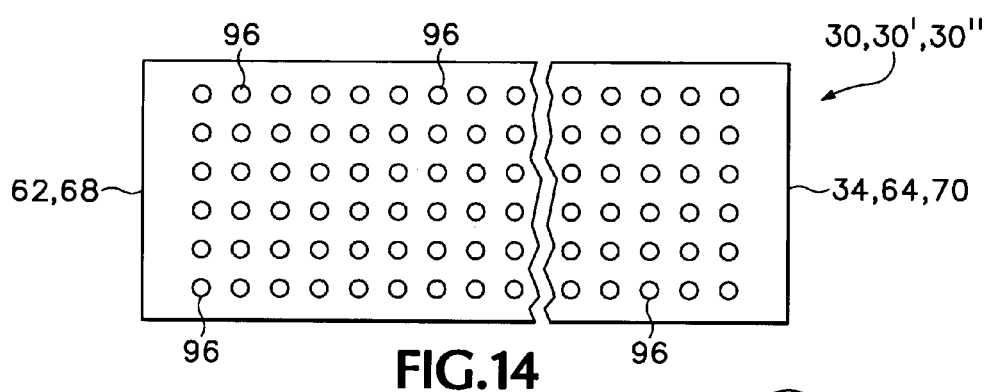
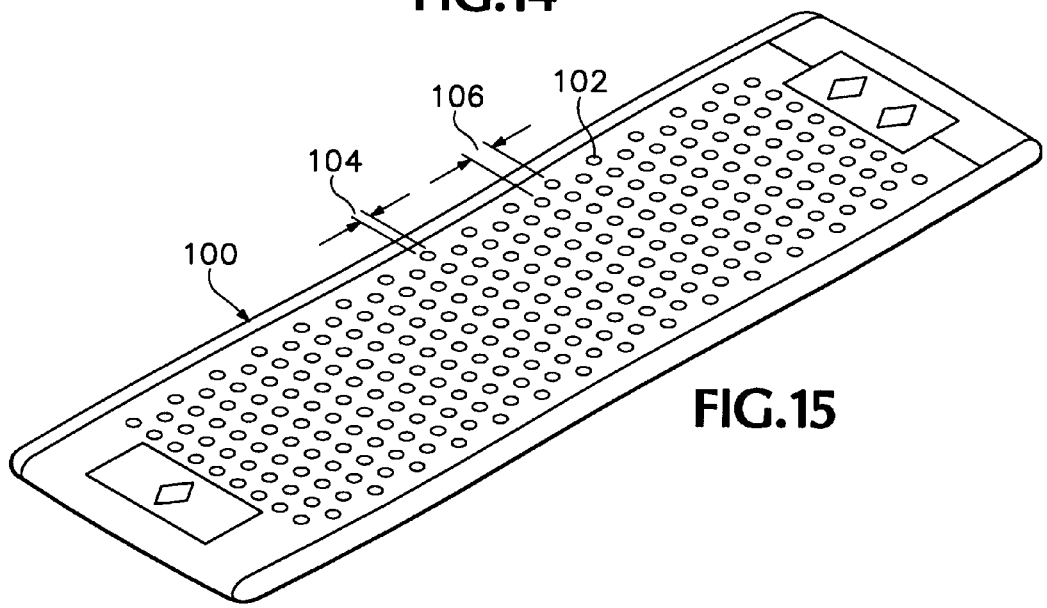

WRIST SPLINT

BACKGROUND OF THE INVENTION

The present invention relates to splints for immobilizing injured body members, and particularly to an improved splint that can be shaped to support a patient's hand, wrist, and forearm in comfort.

Splints for use in emergency and post-operative situations are known, for example, from Scheinberg, U.S. Pat. No. 4,676,233 and U.S. Pat. No. 3,943,923, both of which teach the use of a soft metal sheet formed into a configuration that provides needed support for an injured limb. Bentele U.S. Pat. No. 4,161,175 discloses surgical splints incorporating formed sheet metal or molded plastic bases. Ender U.S. Pat. No. 4,549,537 discloses another splint based on the use of sheet aluminum material. Bolla et al. U.S. Pat. No. 6,039,706 discloses a splint using a sheet of corrugated metal as its principal supporting structure.

Health care professionals have long used splints and casts fashioned out of plaster, fiberglass, preformed metal, or molded thermoplastic materials. These splints are designed to rigidly prevent motion and once formed into position cannot be reformed, for example to accommodate swelling, without considerable difficulty. A plastic or fiberglass splint once cured cannot be reformed. If swelling is excessive, a new fiberglass or plaster splint must be applied or an instrument resembling a large pliers (often referred to as a cast bender) is used to break the plaster or fiberglass material in order to relieve the pressure caused by the swelling. A thermoplastic splint is usually rigid and requires heat in order to be reformed. Preformed metal splints are also quite rigid and difficult to bend or mold. None of the above mentioned splints once formed allow a patient to perform any significant active movement or provide variably controlled active movement.

Active movement in a joint is movement performed by the patient as opposed to passive movement, i.e., movement performed by a physical therapist. Controlled variable active movement is active movement that can be increased or decreased according to the desire of the treating health professional. For example, it is desirable for orthopedic surgeons to vary a patient's allowable active movement during a post-operative convalescent period—i.e., the surgeon might desire less active movement during the first post-operative week and greater movement during the second post-operative week. Today, active movement is thought to be of significant value in the rehabilitation and treatment of fractures and soft tissue conditions. For example, following an open reduction and internal fixation of a distal radial (wrist) fracture orthopedic surgeons frequently direct their patients to remove their splints several times a day for active range of motion exercises. When these splints are removed patients are at increased risk of sustaining an injury. Therefore, it is desirable, to have not only an easily formable splint to accommodate post injury swelling, but a splint capable of allowing variable degrees of active movement while remaining in place.

SUMMARY OF THE INVENTION

The present invention provides an answer to some of the shortcomings of the previously available splints, by providing an easily usable splint that is conveniently storable in a planar configuration prior to preparation for use with a particular patient, and which can be formed to provide comfortable support for a patient's hand, wrist, and forearm with a chosen amount of firmness.

In a first preferred embodiment of the invention, such a splint has a body that includes an elongate flat supportive member, or core, of malleable metal that is more supportive at one end of the splint than at the other end. The same splint then can be used depending on its orientation, to provide either a greater or lesser amount of firmness of support for a patient's wrist, varying the patient's ability to perform active movements.

A layer of padding material is attached to each side of the core, and in one preferred embodiment of the invention an outer cover provides additional comfort and carries indicia to identify the amount of support provided by each end of the splint.

In one preferred embodiment of the invention, the padding material on a skin contact surface, or the splint surface directly adjacent to the skin, referred to herein as the closer face of the splint may preferably be of open-cell synthetic polymeric foam material, and the outer cover on that closer face of the splint is preferably of absorbent fabric that is open to passage of moisture and vapors, so as to maintain the patient's comfort with the splint in contact with the patient's skin.

In one preferred embodiment of the invention, a portion of the outer cover located on the opposite the splint surface not in contact with the skin, or farther face of the splint, is of material adapted to be engaged by the hook-carrying fastener portion of a hook-and-loop fastener system in order to facilitate the attachment of straps used to encircle the patient's hand, wrist, and arm to hold the splint in place.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 2 is a sectional view of the splint shown in FIG. 1 taken along line 2—2.

FIG. 3 is a sectional view taken along line 3—3 of FIG. 1.

FIG. 4A is a side elevational view of an alternative core portion of a splint similar to that shown in FIGS. 1 and 2, taken in the direction indicated by line 2—2 in FIG. 1.

FIG. 4B is a view similar to that of FIG. 4A showing another alternative core member for an orthopedic splint such as that shown in FIGS. 1 and 2.

FIG. 12 is a partially cutaway end view of a splint such as that a shown in FIGS. 1–3, showing one way of forming the splint to provide additional stiffness.

FIG. 13 is a sectional view taken along line 13—13 of FIG. 7.

FIG. 14 is a plan view of a portion of another alternative core for a splint according to the present invention.

FIG. 15 is an isometric view of a splint including an alternative embodiment of the invention.

DETAILED DESCRIPTION OF THE PREFERRED EMBODIMENTS

Figure 1:
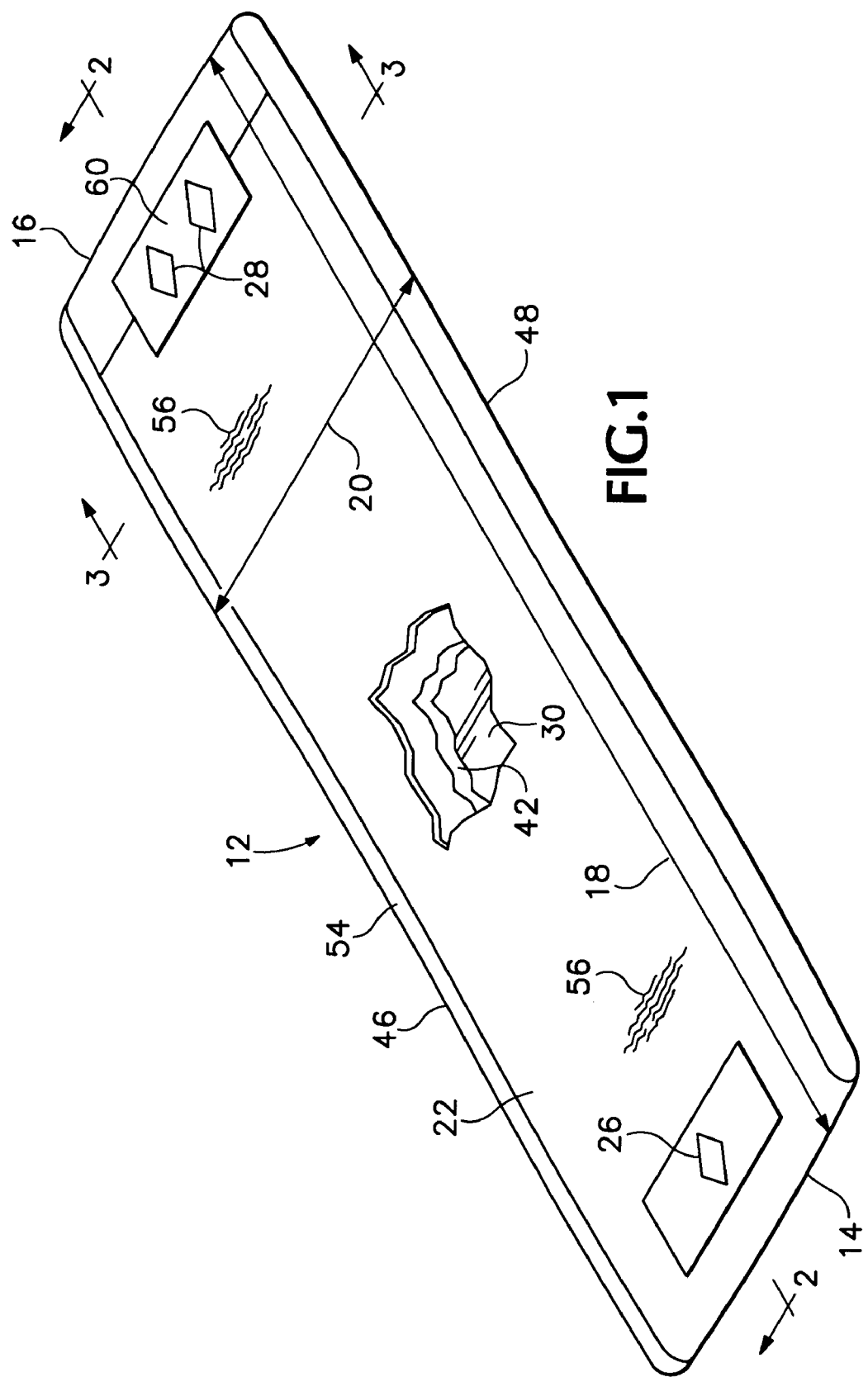
FIG. 1 is an isometric view of an orthopedic splint according to the present invention in a storage configuration.

Referring now to the drawings which form a part of the disclosure herein, in FIGS. 1 and 2 a splint 12 which is a first preferred embodiment of the present invention is shown in a generally planar configuration in which the splint is manufactured and is usually packaged for shipment and for storage prior to its use. A body of the splint 12 has a first end 14 and an opposite second end 16 defining a length 18 that is greater than the width 20. For example, the length 18 may be twelve or fifteen inches and the width 20 may be in the range of four to six inches, and preferably about 4½ inches for a splint 12 intended for use to support the wrist of an adult.

The body of the splint has a skin contact, or closer face 24, intended to be placed in contact with a patient's skin or wound dressing, and shown in FIG. 2, but facing downward in FIG. 1. An opposite or farther face 22 of the splint facing upward, in FIG. 1, and normally faces outward, away from a patient's skin when the splint 12 is in use. The designations as closer and farther faces 24 and 22 thus refer to the proper orientation of the splint 12 with respect to a person's arm, wrist, and hand when the splint 12 is in use.

Identifying indicia are provided on the face 22 of the splint 12, in the form of, for example, a single diamond 26 displayed on the farther face 22 adjacent the first end 14 of the splint 12 and a pair of diamonds 28 or other distinguishable marking provided on the farther face 22 adjacent the second end 16 of the splint 12. The indicia 26 and 28 distinguish the first end 14 from the second end 16, because the construction of the splint, as will be explained presently, provides support for a patient's hand and wrist with a first amount of firmness provided by the structure at the first end 14 of the splint 12 and with a second, greater, amount of firmness provided by the structure of the second end 16 of the splint 12.

The splint 12 as shown in FIGS. 1–3 has a core 30 of malleable metal in the form of a flat sheet whose dimensions are slightly smaller than the length 18 and width 20 of the splint 12.

At the second end 16 of the splint 12, the core 30 includes a thicker portion 34 having a length 36 preferably in the range of about 3 to 6 inches, and preferably of about 4.5 inches, for a splint whose length 20 is in the range of about 9–15 inches, in which the core 30 has a greater thickness, in order for the splint to provide greater firmness. The greater thickness may be provided by folding the aluminum sheet material back upon itself adjacent the second end 16. The length 36 of the thicker portion 34 is thus long enough to provide support for the wrist 76 of an adult. As a result of the greater thickness, the thicker portion 34 of the core 30 adjacent the second end 16 of the splint 12 is stiffer than the portion of the core 30 adjacent the first end 14 of the splint 12. Preferably the core 30 is of nearly pure aluminum such as Aluminum Association Type 1XXX aluminum, and preferably Type 1145 aluminum sheet material (99.45% pure) having a thickness 32 in the range of 0.008 inch–0.025 inch, and preferably having a thickness of about 0.016 inch. Preferably the metal is annealed to a dead soft or "O" temper. Bending the aluminum core 30 during the process of adjusting the splint 12 to conform to a patient creates a curved cross-section that increases the rigidity of the splint, i.e., makes it more resistant to bending.

A farther side layer 42 of padding material and a closer side layer 44 of padding material envelop the core 30 and extend slightly beyond it at each of the first and second ends 14 and 16 and along the opposite longitudinal lateral margins 46 and 48 of the splint 12. The farther side and closer side layers 42 and 48 of padding material are attached to the respective opposite closer and farther sides of core 30 and to each other by respective layers 50 of adhesive material which also interconnects the farther side layer 42 of padding material to the closer side layer 44 of padding material along the margins adjacent the opposite ends 14 and 16 and opposite lateral margins 46 and 48 of the splint 12. Preferably the layers 42 and 44 of padding material extend beyond the margins of the core 30 a distance sufficient to provide comfortable padding. For example, in a splint 12 whose width 20 is 4½ inches the core 30 is 3.9 inches wide, and the layers 42 and 44 of padding material may extend about 3/16 inch beyond the core 30 at each of the first and second ends 14 and 16 and an 1/8 inch beyond the core 30 along each of the lateral margins 46 and 48.

A layer of pressure-sensitive adhesive material, which may be acrylic based, is provided on the surface of each of the layers of polymeric foam material of the farther side layer 42 and the closer side layer 44, protected by a peel-off liner which is removed when the layers 42 and 44 of padding material are attached to the core. This adhesive material becomes the layer 50 mentioned above, in the manufacture of the splint 12.

Enclosing the core 30 and the layers 42 and 44 of padding material is an outer cover 52 of textile fabric. Preferably, the outer cover 52 is made of two different types of fabric, with a first, or closer face part 54 of the outer cover 52 being located on and defining the closer face 24 of the splint 12, and preferably extending around the lateral margins 46 and 48 and onto the farther face 22 a short distance, as seen best in FIGS. 1 and 3. A farther face part 56 of the outer cover 52 is preferably of a different fabric.

The farther side layer 42 of padding material has a thickness 43 preferably in the range of 1/16 inch to ¼ inch, and the thickness 43 is most preferably 1/8 inch. The farther side layer 42 of padding material should be of a somewhat resiliently compressible or elastomeric material, and may be of a polymeric foam such as a closed cell microcellular low density expanded polyethylene available from Voltek Division of Sakisui American Corporation as its Volara Type A foam, with a layer of a flexible pressure-sensitive adhesive material already applied to one side of the foam to serve as the layer of adhesive 50.

Such foam material used as the farther side layer 42 preferably has a density of at least about 1.5 lbs. per cubic foot and preferably at least 2.0 lbs. per cubic foot. Greater densities, up to at least about 4 lbs. per cubic foot are desirable, but are considerably more expensive.

The closer side layer 44 of padding material in a preferred embodiment of the splint 12 has a thickness 45 of about ¼ inch, although a thickness 45 in the range of ⅛ inch to ⅜ inch is acceptable. The closer side layer 44 of padding material should also be somewhat resiliently compressible, and is preferably porous. Therefore, the layer 44 is preferably of open-cell polymeric foam, such as a polyurethane foam, with an applied layer of flexible pressure sensitive adhesive. An acceptable density for such foam material is 1.0–4.0 lbs. per cubic foot, with 1.5 lbs.–3.0 lbs. per cubic foot being preferred. An indentation load deflection of about 75 is preferred, but any value in the range of 25 to 150 is acceptable, to provide sufficient firmness yet be comfortable. The open-cell construction of the closer side layer 44 of padding material allows sufficient circulation of air, to cool and to dissipate evaporation from the skin of a patient using the splint 12, in order to provide ample comfort for a patient using the splint 12. One acceptable material for the closer side layer 44 is available from Foamex, of Compton, Calif., as its Foam Grade F 145 44 F.6 FA 44145-304.

Preferably, the closer face part 54 of the outer cover 52 is made of a soft, absorbent fabric with a significant amount of elasticity in at least the transverse direction, indicated by the arrow 55 in FIG. 3. For example, a brushed terrycloth or boucle fleece of 65 percent polyester and 35 percent rayon fiber of 100 denier yarn, available from Eclat Textile Co. Ltd. of Industry, Calif. as its product number 1206D performs well for absorbing moisture and exudate from a patient's skin. Preferably, such a cloth is a low loop, tightly knitted material, brushed to provide a soft and slightly matted surface which is absorbent and not abrasive, so that the splint 12 can be used comfortably in direct contact with the patient's skin.

The elasticity of the fabric of the closer face part 54 of the outer cover 52 allows the closer side layer 44 of padding material to conform easily to a patient's hand, wrist, and arm without the fabric of the closer face part 56 being pulled free from the closer side layer 44 of padding material when it is compressed irregularly by conforming to the shape of the patient's hand, wrist, and forearm.

The farther face part 56 of the outer cover 52, located on and defining a part of the farther face 22, is preferably of a material which is receptive to the hooked material portion of a hook-and-loop fastening material such as that commonly known under the trademark Velcro® or an equivalent "thistle-cloth" fastener material. Preferably the fabric of the farther face part 56 is significantly less elastic than the fabric of the closer face part 54, in order better to resist separating from the foam material of the farther side layer 42 of padding material when such a hooked fastener material is disconnected from the farther face part 56 of the outer cover 52. The farther face part 56 of the outer cover 52 extends from the first end 14 of the splint toward the second end 16, and extends over most of the width 20 of the splint 12, from one to the other of the margins of the closer face part 54 of the outer cover 52, as shown in FIGS. 1 and 3. Adjacent the second end 16 of the splint, a small piece 58 of the material of the farther face part 56 may be attached to the material of the closer face part 54 at the second end 16, to extend toward the first end 14 of the splint, slightly overlapping a portion of the main piece of the farther face part 56 to leave a slot at the second end 16 through which the core 30 and layers 42 and 44 of padding material may be inserted into the outer cover 52. Thereafter, a label 60 including indicia such as the previously mentioned pair of diamonds 28 is fastened in place, preferably by a heat-activated adhesive, to secure the outer cover 52. A label including the indicia 26 may also be attached in the same manner. A suitable material for the farther face part 56 of the outer cover 52 is a brushed nylon tricot such as is available from the Fabrite Laminating Corporation of Wood-Ridge, N.J. as its style 5437 material, which is a warp knit fabric of 32 gauge, using 40 denier yarn to produce cloth having a weight of 2.04 ounces per square yard and a finished thickness of 0.035 inch. This cloth provides ample protection for the farther side layer 42 of padding material and is strong enough to receive and be engaged by the hook portion of a hook-and-loop fastener material appropriate for fastening straps to attach the splint 12 to a patient's arm 78. The material is stable enough in size not to stretch excessively when the hooked fastener material is removed. As a result, removal of the fastener materials to disconnect straps from the splint does not unduly tend to separate the material from the farther side layer 42 of padding material. The outer cover 52 is attached to the adjacent surfaces of the layers 42 and 44 of padding material by the use of a layer of fusible heat-activated fabric adhesive, activated after the core 30 and layers of padding material 42 and 44 have been placed within the outer cover 52. Preferred fusible fabric adhesives are available from Freudenberg Nonwovens, of Durham, N.C., under the trademark Pellon®, as its product number 807 Wonder-Web™ fusible web and its product number 725 heavy-duty Wonder-Under® fusible web. The web of fusible adhesive is porous and once activated continues to permit free movement of moisture and vapor through the outer cover and the open-cell material of the closer side layer 44 of padding material.

Referring to FIGS. 4A and 4B, instead of the core 30 of sheet aluminum of which a portion 34 is folded back as shown in FIG. 2, a core 30' may be of aluminum formed, possibly by extrusion, to include a first portion 62 corresponding to the single thickness portion of the core 30 shown in FIG. 2 for the first end 14 of the splint 12, a thicker second portion 64, with a thickness generally corresponding with the doubled portion 34 of the core 30 for the second end 16 of the splint 12, and a tapered transitional portion 66. The thicker part 64 thus provides the desired greater firmness for the second end 16 of a splint 12 including the core 30'.

Alternatively, as shown in FIG. 4B, a core 30" may be uniformly and gradually tapered from a thinner end 68 to a thicker end 70, to provide greater firmness at the second end 16 of a splint 12 including the core 30" with its thicker end 70 located at the second end 16.

Figure 5:
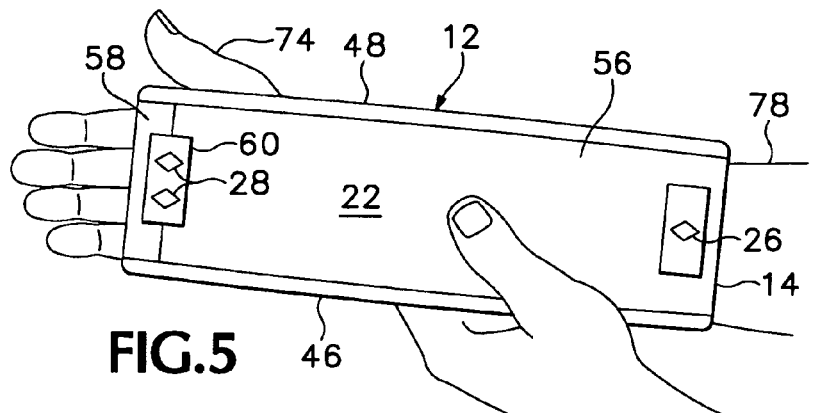
FIG. 5 is a pictorial view showing a splint such as the one shown in FIG. 1 adjacent the volar side of a patient's hand, wrist, and forearm before being shaped to fit the patient.

The splint 12 is prepared and used as depicted in FIGS. 5, 6, 7, and 8 in order to provide a desired level of support for an injured patient's hand 74, wrist 76, or forearm 78. If a moderate degree of immobilization and support is desired, the first end 14 of the splint 12, identifiable by the single diamond 26 or other indicium, is placed alongside the patient's hand, with the second end 16 extending toward the patient's elbow. Alternatively, if a greater degree of support and immobilization of the wrist and hand is desired, the second end 16 is placed adjacent to the hand 74, as shown in FIG. 5, while the first end 14 is placed alongside the patient's forearm 78. In either case the closer face 24 of the splint 12 should be directed toward the volar side of the patient's arm, usually in direct contact therewith.

Figure 6:
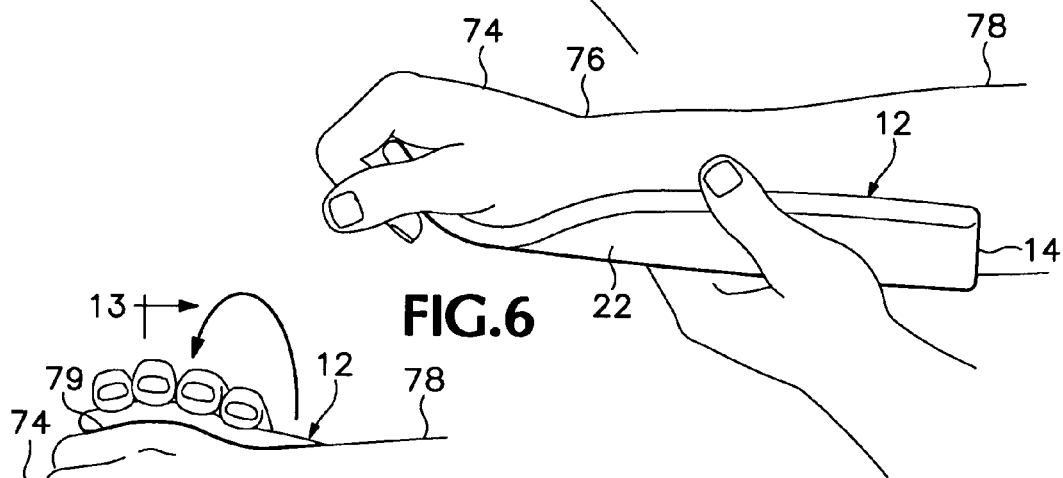
FIG. 6 is a pictorial view showing the splint shown in FIG. 5 in the process of being shaped to the configuration necessary for use.

In order to provide the required amount of support, the splint 12 must be shaped to conform to the patient's hand 74, wrist 76, and forearm 78. This is accomplished manually by the attending medical personnel, by first bending the splint 12 to conform generally to his or her own wrist and hand. The splint 12 is placed with the chosen end 14 or 16 nearer the patient's hand, and with the distal farther face 22 directed away from the hand 74 and forearm 78, as shown in FIG. 5, and the attending medical professional pushes on the splint 12, shaping it to conform roughly to his or her arm, as illustrated in FIG. 6. This results in the core 30 bending to assume and retain the required shape. The end portion 14 or 16 of the splint 12 adjacent the ulnar side 79 of the hand 74 is also bent upward around the hand 74 as indicated by the arrow in FIG. 7, to provide additional support and fit smoothly.

The attending person can then adjust the shape of the splint 12 to fit the patient more precisely by pushing with the thumbs against the closer face 24 while the fingers press on the farther face 22 of the splint 12. The end 14 or 76 of the splint 12 is that located within the patient's hand 74 may also be bent downward in the form of a small roll, if desired, to support the patient's fingers in a comfortable attitude, preferably using a splint 12 whose length 18 is ample. The relatively thin and firm padding material of the farther side layer 42 enables the attending person to feel the shape to which the core 30 is being bent and allows him or her to manipulate the core 30 precisely to conform as desired to the patient's hand 74, wrist 76, and arm 78. Since the core 30 is preferably annealed to be deadsoft for initial manufacture of the splint, it is initially easy to bend the core into the desired form. The required form of the splint 12 has a bending curved cross-section that provides improved rigidity by acting structurally as a "C"-shaped channel.

Figure 8:
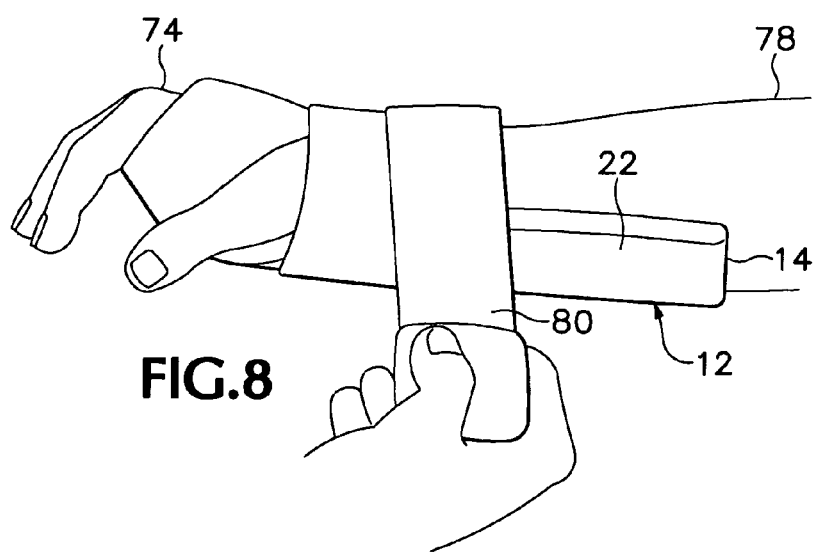
FIG. 8 is a pictorial view showing the application of an elastic wrap to secure the splint shown in FIGS. 5–7 to the patient's hand, wrist and arm.

Once the shape of the splint 12 has been properly adjusted to fit the patient, the splint is put into place as shown in FIG. 8, with the closer face 24 of the splint facing toward the volar aspect of the patient. The splint 12 is secured in place by wrapping the patient's hand 74, wrist 76, and arm 78, and the splint 12 with an elastic bandage 80 as shown in FIG. 8.

Figure 9:
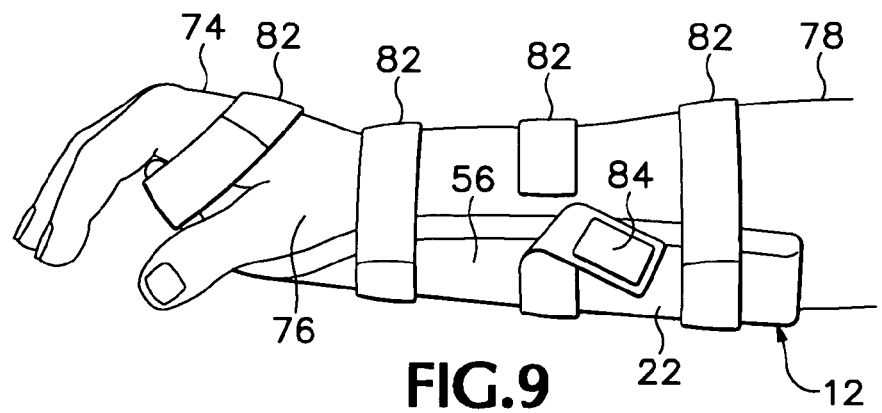
FIG. 9 is a view similar to that of FIG. 8, but showing the use of straps fastened by hook-and-loop fasteners to secure the splint to a patient's hand and arm.

Alternatively, as shown in FIG. 9, the splint 12 may be held in place by wrapping it with flexible straps 82 provided with hook-and-loop fasteners. Patches 84 of the hook portion of such hook-and-loop fastener material may be engaged in the material of the farther face part 56 of the outer cover 52 as shown in FIG. 9. Because of the nature of the fabric preferably used as the farther face part 56 of the outer cover 52 removal of the fastener material, as for adjusting the shape 82, does not significantly degrade the material of the farther face part 56 or pull it apart from the underlying farther side layer 42 of padding material.

Figure 10:
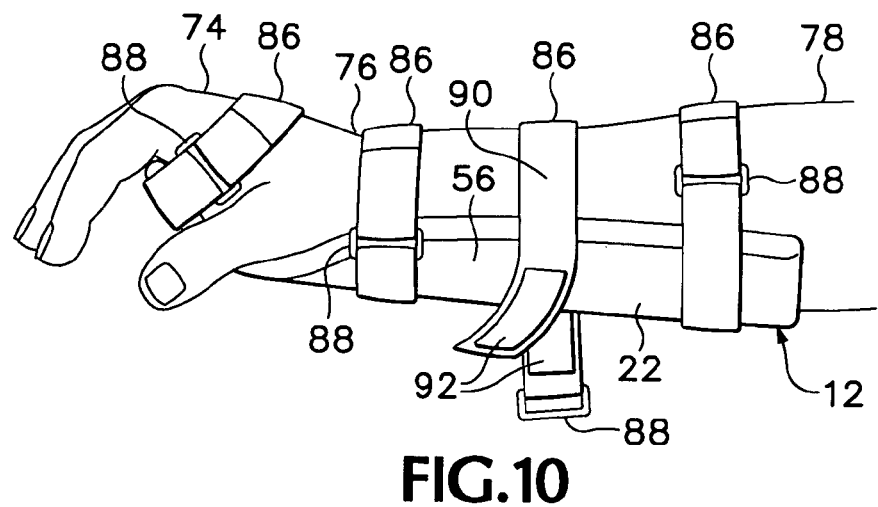
FIG. 10 is a view similar to FIG. 9, but showing the use of straps equipped with D-rings and hook-and-loop fasteners to secure the splint to a patient's arm.

Alternatively, as shown in FIG. 10 flexible separate straps 86 equipped with D-rings 88 and hook-and-loop fastener materials 90 and 92 may be placed around the patient's hand 74, wrist 76, and arm 78 and the splint 12, and if desired the hooked portion 92 of the fastener material may be engaged with the fabric of the farther face part 56 of the outer cover 52.

Figure 11:
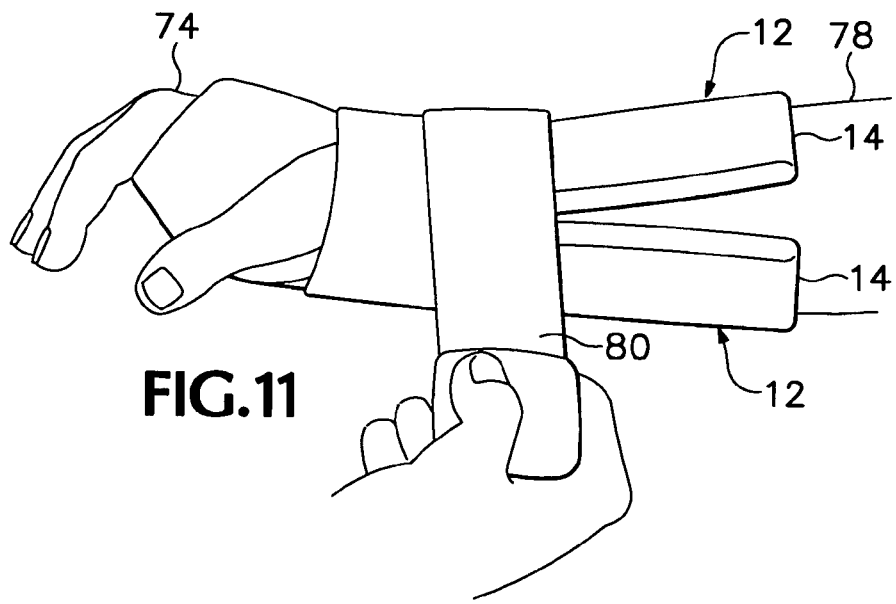
FIG. 11 is a view showing the use of a pair of splints such as that shown in FIGS. 1 and 2 in a clam-shell arrangement on a patient's wrist and arm.

As mentioned above, use of the splint 12 with the second end 16 adjacent the patient's hand 74 and wrist 78 gives greater support than use of the splint 12 with the first end 14 adjacent the hand 74 and wrist 76. In a situation where maximum immobilization of a patient's hand 74 and wrist 76 is required, a pair of splints 12 may be applied simultaneously to both the volar and dorsal sides of the patient's arm 78, as shown in FIG. 11. The two splints 12 are both shaped separately to conform to their respective intended positions and then both are secured to the patient in generally the same manner described above with respect to a single splint 12.

Figure 7:
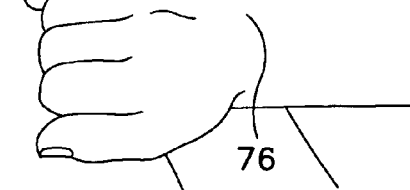
FIG. 7 is a pictorial view showing how the splint shown in FIGS. 5 and 6 is bent further to conform to the ulnar side of a patient's hand.

In some cases, it may be desired to provide additional stiffness in the portion of the splint 12 along the patient's arm 78 by bending the splint outward to form side flanges 94 along the side margins 46 and 48 as shown in cross-section view in FIG. 12. The degree of stiffness in either end 14 or 16 of the splint can be varied most easily by folding such a portion of the splint. It is desirable in particular to bend a portion along the lateral margin 46 or 48 which is to be located on the ulnar, or little finger side of the patient's wrist 76 and forearm 78 into the form of a flange 95 along the ulnar side 79, as shown in FIGS. 7 and 13, to provide added stiffness to the splint 12 and thus provide additional firmness of support, in direct proportion to the length and depth of the portion thus formed into a flange 95.

As shown in FIG. 14, the core 30, 30', or 30" may be perforated, providing ventilation through an array of holes 96. The holes 96 cooperate with the absorbent material of the closer face part 54 of the outer cover 52, and with the closer side layer 44 of padding material, to provide comfort by promoting ventilation and facilitating cooling and evaporation of perspiration from the patient's skin. When a perforated core is used, an open-cell foam similar to that described for use as the closer side layer 44 may also be used for the farther side layer 42.

Referring to FIG. 15, a splint 100 is similar to the splint 12, except that it is perforated by holes 102, arranged in a regular pattern. The holes 102 may be circular, with diameters 104 in the range of 1/32 inch to 1/8 inch, for example, and spaced apart by a distance 106, of 1/2 inch to 1 inch, to provide comforting ventilation without significantly weakening the splint.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An orthopedic splint for use on a person's wrist, comprising:
   (a) an elongated body having opposite first and second ends and an elongated core of malleable metal having a pair of opposite initially generally planar sides;
   (b) a respective layer of flexible and resilient padding material covering each of said opposite sides; and
   (c) an outer cover of a textile fabric enclosing said core and said layers of padding material, said splint having a first firmness adjacent said first end and a second, greater, firmness adjacent said second end thereof.

2. The splint of claim 1 wherein said core has a first thickness adjacent said first end and a greater second thickness adjacent said second end.

3. The splint of claim 1 wherein said core is of sheet metal having a uniform thickness, said sheet metal being doubled back upon itself over a predetermined length of said core adjacent said second end.

4. The splint of claim 1 wherein said respective layers of padding material are attached to said core by an adhesive.

5. The splint of claim 1 wherein each said layer of padding material is adhesively attached to a respective one of said opposite sides of said core, said splint having a closer face associated with a first one of said opposite sides and a farther face associated with the other of said opposite sides of said core, said layer of padding material of said closer face being thicker than said layer of padding material of said farther face.

6. The splint of claim 5 wherein said respective layer of padding material covering said closer side of said core is of open-cell polymeric foam.

7. The splint of claim 1 wherein said core is perforated.

8. The splint of claim 7 wherein said respective layer of padding material covering said farther side of said core is of open-cell polymeric foam.

9. The splint of claim 6 wherein said respective layer of padding material covering said farther side of said core is of closed-cell polymeric foam.

10. The splint of claim 1 wherein said pair of opposite sides of said core correspond respectively to a closer face and a farther face of said splint, and wherein a portion of said outer cover defining said closer face is of substantially elastically extensible fabric.

11. The splint of claim 10 wherein said portion of said outer cover defining said closer face is of an absorbent fabric.

12. The splint of claim 10 wherein said outer cover includes a farther face portion defining a portion of said farther face of said splint, said farther face portion being of material that is substantially inelastic and that is operatively receptive to engagement by a hook material portion of a hook-and-loop fastener.

13. An orthopedic splint for use on a person's wrist, comprising:
   (a) an elongated body having opposite first and second ends and opposite closer and farther faces;
   (b) a core of malleable metal within said body having a pair of opposite initially generally planar closer and farther sides;
   (c) a respective layer of flexible and resilient padding material covering each of said opposite sides of said core, said layer of padding material covering said closer side of said core being thicker than said layer of padding material covering said farther side of said core; and
   (d) an outer cover of a textile fabric enclosing said core and said layers of padding material.

14. The splint of claim 13 wherein said layer of padding material covering said closer side of said core is absorbent.

15. The splint of claim 14 wherein said layer of padding material covering said closer side of said core is of open-cell polymeric foam.

16. The splint of claim 15 wherein said layer of padding material covering said farther side of said core is of closed-cell polymeric foam.

17. The splint of claim 15 wherein said core is perforated.

18. The splint of claim 17 wherein said respective layer of padding material covering said farther side of said core is of open-cell polymeric foam.

19. An orthopedic splint for use on a person's wrist, comprising:
   (a) a body having opposite first and second ends and a pair of opposite closer and farther faces;
   (b) a core of malleable metal within said body having a pair of opposite initially generally planar closer and farther sides;
   (c) a respective layer of flexible and resilient padding material covering each of said opposite sides of said core; and
   (d) an outer cover of a textile fabric enclosing said core and said layers of padding material, said pair of opposite sides of said core corresponding respectively to said closer face and said farther face of said splint, and a portion of said outer cover located on said closer face being of substantially extensible elastic fabric.

20. The splint of claim 17 wherein said portion of said outer cover located on said closer face is of an absorbent fabric.

21. The splint of claim 18 wherein a portion of said outer cover located on said farther face is of material that is relatively inelastic and is operatively receptive to engagement by a hook material portion of a hook-and-loop fastener.

22. The splint of claim 19 wherein said core is perforated.

23. The splint of claim 19 wherein each said layer of padding material is of open-cell polymeric foam.

\* \* \* \* \*